(12) United States Patent
Bonne et al.

(10) Patent No.: US 7,654,129 B2
(45) Date of Patent: Feb. 2, 2010

(54) SENSOR WITH AN ANALYTE MODULATOR

(75) Inventors: Ulrich Bonne, Hopkins, MN (US); Martin John Willett, Portsmouth (GB); Keith Francis Edwin Pratt, Portsmouth (GB); Jerry W. Evans, Houston, TX (US)

(73) Assignee: Honeywell International Inc., Morristown, NJ (US)

( * ) Notice: Subject to any disclaimer, the term of this patent is extended or adjusted under 35 U.S.C. 154(b) by 274 days.

(21) Appl. No.: 11/738,853

(22) Filed: Apr. 23, 2007

(65) Prior Publication Data

US 2008/0163674 A1 Jul. 10, 2008

Related U.S. Application Data

(63) Continuation-in-part of application No. 11/383,738, filed on May 16, 2006, now Pat. No. 7,578,167, application No. 11/738,853, which is a continuation-in-part of application No. 11/383,723, filed on May 16, 2006, now Pat. No. 7,502,109, application No. 11/738,853, which is a continuation-in-part of application No. 11/383,663, filed on May 16, 2006.

(60) Provisional application No. 60/866,182, filed on Nov. 16, 2006, provisional application No. 60/833,190, filed on Jul. 25, 2006, provisional application No. 60/681,776, filed on May 17, 2005, provisional application No. 60/743,486, filed on Mar. 15, 2006.

(51) Int. Cl.
*G01N 25/00* (2006.01)

(52) U.S. Cl. ..................... 73/23.21

(58) Field of Classification Search ............... 73/23.31, 73/31.05
See application file for complete search history.

(56) References Cited

U.S. PATENT DOCUMENTS 4,502,321 A * 3/1985 Zuckerman ............... 73/25.03

(Continued)

FOREIGN PATENT DOCUMENTS

DE 10159616 6/2003

(Continued)

OTHER PUBLICATIONS

Bonne, "High-Speed Gas Analysis with PHASED MGA Gen.1 on NeSSI," Honeywell Laboratories, DOE Sensors & Automation 2006 Annual Portfolio Review, 22 pages, 2206.

(Continued)

*Primary Examiner*—John Fitzgerald
(74) *Attorney, Agent, or Firm*—Kris T. Fredrick

(57) ABSTRACT

A sensor system having an analyte modulator, detector and a pump. The concentration of an analyte sample may be modulated at one time constant. The detector may have an output with a drift at another time constant. The one time constant may be shorter than the latter time constant. The latter time constant may be substantially removed from the detector output with a discriminator. A reservoir may receive high concentrations of analyte from the modulator, before analyte is forwarded to the detector and pump via analyte conveyance lines and valving. The modulation or pre-concentration of analyte in the sensor system may entail shorter times and smaller volumes than those needed by the detector. Such mismatches may be alleviated via accumulation of analyte in the reservoir prior to being forwarded to the detector.

19 Claims, 17 Drawing Sheets

U.S. PATENT DOCUMENTS

| | | | |
|---|---|---|---|
| 5,095,263 A * | 3/1992 | Peters | 324/76.44 |
| 5,112,455 A * | 5/1992 | Cozzette et al. | 205/778 |
| 5,375,979 A | 12/1994 | Trah | |
| 5,722,449 A | 3/1998 | Heinonen et al. | |
| 5,741,413 A | 4/1998 | Capetanopoulos | |
| 5,761,952 A | 6/1998 | Gilby et al. | |
| 6,076,523 A | 6/2000 | Jones et al. | |
| 6,393,894 B1 * | 5/2002 | Bonne et al. | 73/23.2 |
| 6,432,721 B1 | 8/2002 | Zook et al. | |
| 6,750,796 B1 * | 6/2004 | Holloway et al. | 341/143 |
| 6,837,118 B2 | 1/2005 | Bonne et al. | |
| 7,000,452 B2 | 2/2006 | Bonne et al. | |
| 7,075,475 B1 * | 7/2006 | Wan | 341/172 |
| 7,114,366 B1 * | 10/2006 | Jones et al. | 73/1.01 |
| 7,224,285 B2 | 5/2007 | Tiwet et al. | |
| 7,257,986 B2 * | 8/2007 | Haupt et al. | 73/23.2 |
| 2004/0194628 A1 | 10/2004 | Mitra | |
| 2005/0199037 A1 | 9/2005 | Gokhfeld | |
| 2005/0229675 A1 | 10/2005 | Haupt et al. | |
| 2007/0107492 A1 * | 5/2007 | Lasalandra et al. | 73/1.88 |

FOREIGN PATENT DOCUMENTS

| | | |
|---|---|---|
| DE | 10245947 | 4/2004 |
| GB | 2194639 | 3/1988 |
| JP | 6272075 | 9/1994 |
| WO | 0014531 | 3/2000 |
| WO | 0140793 | 6/2001 |
| WO | 2005108953 | 11/2005 |

OTHER PUBLICATIONS

Bonne et al., "Stationary Phase Films for Micro Analytical Measurements," PittCon 2005, Orlando, Fl, Paper 420-1, pp. 1-25, Feb. 27-Mar. 4, 2005.

Captuer, "Mixed Metal Oxide Sensors," 6 pages, Jun. 2003.

Kim et al., "Integrated Peristaltic 18-Stage Electrostatic Gas Micro Pump with Active Microvalves," Solid State Sensors, Actuators, and Microsystems Workshop, Hilton Head Island, South Carolina, pp. 292-295, Jun. 4-8, 2006.

* cited by examiner

SENSOR WITH AN ANALYTE MODULATOR

This application claims the benefit of U.S. Provisional Patent Application No. 60/866,182, filed Nov. 16, 2006. U.S. Provisional Patent Application No. 60/866,182, filed Nov. 16, 2006, is hereby incorporated by reference.

This application claims the benefit of U.S. Provisional Patent Application No. 60/833,190, filed Jul. 25, 2006. U.S. Provisional Patent Application No. 60/833,190, filed Jul. 25, 2006, is hereby incorporated by reference.

This application is a continuation in-part of U.S. patent application Ser. No. 11/383,738, filed May 16, 2006, which claims the benefit of U.S. Provisional Application No. 60/681,776, filed May 17, 2005, and claims the benefit of U.S. Provisional Application No. 60/743,486, filed Mar. 15, 2006. This application is a continuation in-part of U.S. patent application Ser. No. 11/383,723, filed May 16, 2006, which claims the benefit of U.S. Provisional Application No. 60/681,776, filed May 17, 2005, and claims the benefit of U.S. Provisional Application No. 60/743,486, filed Mar. 15, 2006. This application is a continuation-in-part of U.S. patent application Ser. No. 11/383,663, filed May 16, 2006, which claims the benefit of U.S. Provisional Application No. 60/681,776, filed May 17, 2005, and claims the benefit of U.S. Provisional Application No. 60/743,486, filed Mar. 15, 2006.

U.S. patent application Ser. No. 11/383,663, filed May 16, 2006, is hereby incorporated by reference. U.S. patent application Ser. No. 11/383,723, filed May 16, 2006, is hereby incorporated by reference. U.S. patent application Ser. No. 11/383,738, filed May 16, 2006, is hereby incorporated by reference. U.S. Provisional Application No. 60/681,776, filed May 17, 2005, is hereby incorporated by reference. U.S. Provisional Application No. 60/743,486, filed Mar. 15, 2006, is hereby incorporated by reference.

BACKGROUND

The present invention pertains to instrumentation and particularly to sensors. More particularly, the invention pertains to fluid and chemical sensors.

U.S. Pat. No. 6,393,894, issued May 28, 2002, is hereby incorporated by reference. U.S. Pat. No. 6,837,118, issued Jan. 4, 2005, is hereby incorporated by reference. U.S. Pat. No. 7,000,452, issued Feb. 21, 2006, is hereby incorporated by reference. These patents may relate to aspects of structures and processes related to fluid analyzers.

SUMMARY

The invention is a chemical sensor having analyte modulation.

DESCRIPTION

Figure 1:
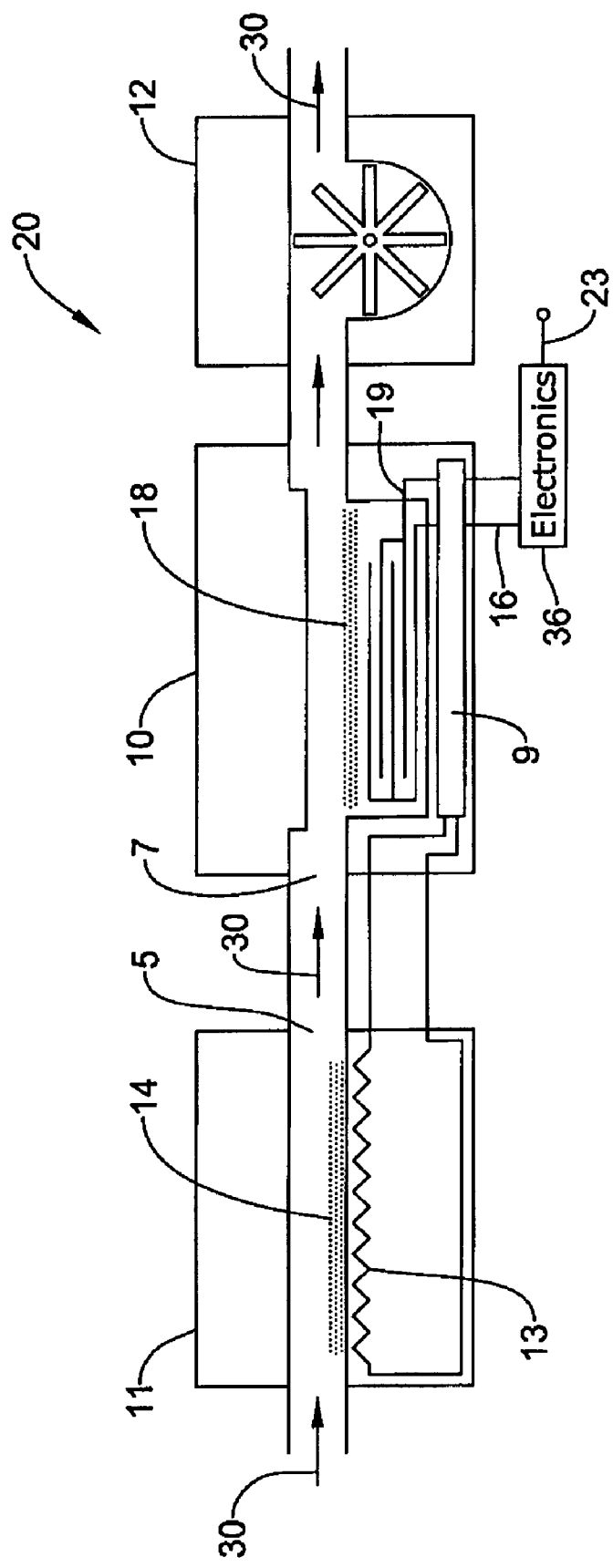
FIG. 1 is a diagram of a sensor with an analyte modulator.

FIG. 1 is a diagram of a sensor system 20 having a sensor 10 along with an analyte modulator 11 having an output 5 connected to an input 7 of the sensor 10, and a pump 12, showing how baseline drift is eliminated by creating and presenting to the sensor 10 a modulated analyte concentration, which enables a long time constant drift or low-frequency drift (perhaps cyclic) to be separated or filtered out according to time constant or frequency. (In some scenarios, one may note a relationship between time constant and cut-off frequency of certain filters.) Then the sensor system 20 may be able to detect certain fluids and provide good quantitative measurements of various parameters of a sample analyte 30. The sensor 10 may utilize a structure of an electrochemical sensor; however, this structure is just an illustrative example since another kind of sensor may be used instead.

A principle of invention may involve time constant or frequency discrimination. Sensor or detector 10 may be provided with the analyte concentration modulator 11 (based on analyte adsorption and thermal desorption) to generate concentration amplitude modulation in time that is of a high frequency or short time constant relative to a frequency or time constant associated with baseline drift. The base line drift may be unidirectional and not have a repetitive sequence, cyclic pattern or reset manner. Therefore, signals with the latter frequency or time constant may be eliminated with a short time constant or high frequency retention or pass mechanism or discriminator 9 that retains the signal with the shorter time constant or higher frequency. The mechanism may often be an electronic device such as a high-pass filter, a time constant discriminator 9, AC coupler, or synchronous amplifier. Other kinds of devices may be used to effect a separation or discrimination of signals of drift and modulation, having different time constants or frequencies, respectively, and to retain the either type of signals for instrumentation purposes. In the case of removing drift signals for the present sensor output, there may be an improvement of sensor signal stability and sensitivity.

A distinction of the present invention may be a use of an adsorption/desorption approach to generate analyte concentration modulation to stabilize an output signal 16 of the sensor 10, while also serving to increase its sensitivity or minimum detection limit (MDL) and its capability to serve as dosimeter.

Some sensors, while being sensitive and selective, may still be of unacceptable reliability if they suffer from unpredictable baseline drift, just fall short of customers' expectations for even better sensitivity, or feature dead volumes too large or response times too long to take an advantage of PHASED-available 100-500-nL pre-concentrated analyte pulses of 10-50 ms in half-width. "PHASED" may be phased heater array structure for enhanced detection.

The modulator 11 may be a PHASED PC. However, the analyte adsorber 14 of a modulator 11 at a front end of the present sensor system 20 (FIGS. 1, 3 and 4) does not need to be limited to a PHASED chip, but may include a coated non-MEMS capillary, a packed capillary or other absorbers that can release the adsorbed analyte via a thermal pulse.

Types of drift may include baseline drift and span drift. The drifts may be caused by a change in sensitivity of a sensor, e.g., output per analyte input concentration. Modulation approaches may remove the baseline drift but not necessarily the span drift. To eliminate span drift, one may need an analyte "puff" of known concentration. Feasibility may be dependent on having a sensor dead-volume that is not inordinately larger than the volume of the modulation "puffs" of analyte 30.

Figure 2:
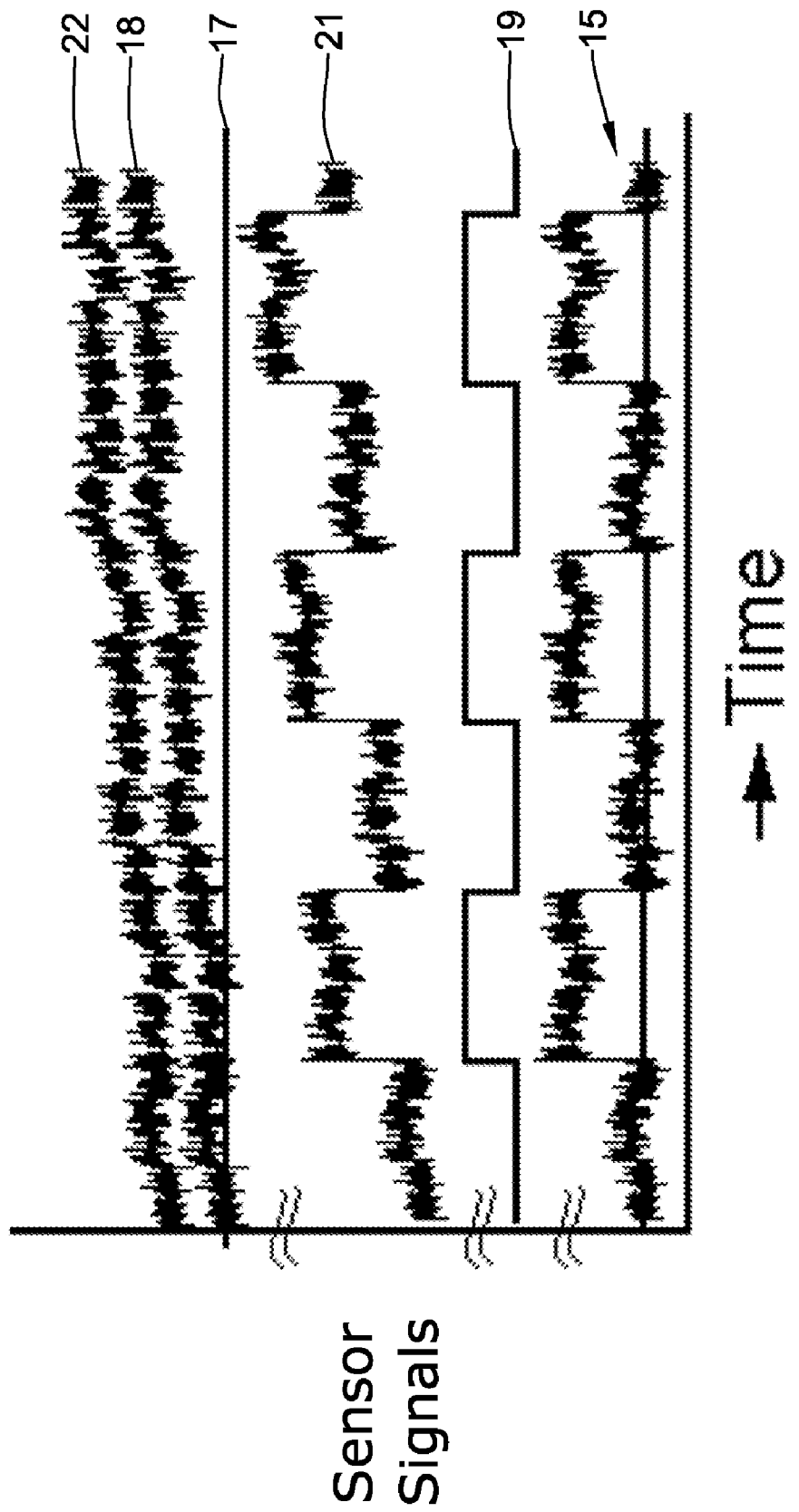
FIG. 2 is a sensor signals versus time chart for the sensor of FIG. 1.

Solutions to some of these issues may include generating analyte concentration (or mass-flow) modulation upstream of the sensor 10, so that the sensor output 16 can show a corresponding AC signal component. To generate such modulation, an adsorber film 14 may be provided with a heater 13, as shown in FIG. 1. By filtering out the slower baseline drift, only the AC part of the sensor signal 15 may be used as sensor output 16, as illustrated at the bottom of the sensor signals versus time chart of FIG. 2. Sensor 10 may have a permeable membrane 18 situated between a fluid flow 30 and a detector 19.

To enable the available but fast and low-peak volume PHASED preconcentrator to work with available sensors, the analyte pulses provided by the modulator 13 may be mechanically stored in a reservoir 24 (FIG. 3) for subsequent quantification (and then electronic integration in time) and form the basis for the sensor 10 to serve as an analyte dosimeter having improved MDL, improved sensor signal stability and being able to overcome dead volume mismatches.

Several ways of generating the analyte concentration modulation, other than with PHASED pre-concentration (PC) chips, may be utilized, such as state-of-the-art "Tenax™ tubes" used in the general chromatography (GC) community to preconcentrate sample analytes, and ice- or liquid-$N_2$ cooled cold-traps. PHASED PC (pre-concentrator) chips may have the advantage of requiring less space, power and time, but also of generating little analyte volume in a brief time, which may be too short for many other sensors. Some adjustments may need to be made for the other sensors.

For the one or more sampling pumps 12, one may use appropriate off-the-shelf pumps. The details of such an analyte concentration-modulating PC 11 are shown in FIG. 1. The baseline of an ideal sensor does not drift as indicated by trace 17 in FIG. 2. However, real sensor baselines may tend to typically drift as represented by trace 18. To overcome the effects of such drift, one may set the control of a PC 11 to adsorb and release analyte 30 at periodic intervals, as controlled by its embedded heater 13, as represented by trace 19. Such intervals of trace 19 may be selected to be commensurate with the sensor's response time, so that when some small concentration of analyte 30 is present, the sensor output 16 resembles trace 21 rather than 22, somewhat above the baseline.

After the sensor output 16 has dropped to near-(drifting) baseline as a result of lacking analyte during the PC adsorbing period, the PC heater 13 may be energized and the analyte 30 is desorbed and released, generating a step-up in sensor signal 16, until substantially all analyte 30 retained by the PC 11 is desorbed, the heater 13 is turned off and the cycle can start again, giving rise to trace 21, with a chopped value riding on the drifting baseline. By feeding the chopped signal of trace 21 to suitable signal processing electronics 36 such as a high (frequency) pass filter, AC coupled amplifier or a synchronous amplifier, the slow-changing baseline drift component, even if not repetitive or cyclic, may be eliminated resulting in a signal 23 represented by trace 15, which is substantially free of the baseline drift effect and thus allows one to reliably measure down to smaller concentrations with the sensor 16. Distinguishing between the drift and modulated signals may be done according to the lengths of their respective time constants. A primary concern here is to deal with baseline drift and not necessarily with span drift.

Figure 3:
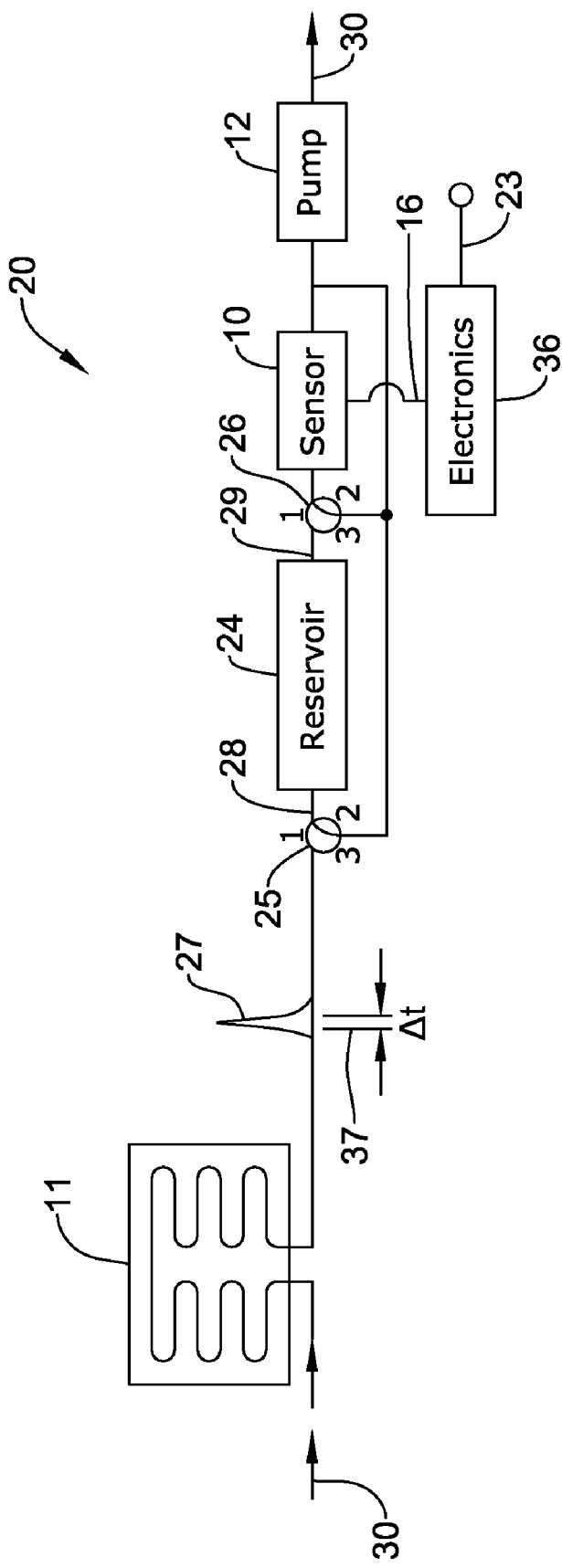
FIG. 3 is a diagram of a sensor system having a pre-concentrator analyte modulator arrangement with a reservoir.

If the available, preconcentrated analyte volume is still too small for sensor 10, FIG. 3 may present an approach based on the combination of a PC 11 with a storage reservoir 24, into which several injections of PC'd analyte 30 can be made. System 20 of FIG. 3 may solve a problem of non-commensurate response times between PC 11 and sensor 10 by using a reservoir 24 and valves 25 and 26.

FIG. 3 is a diagram of pre-concentration arrangement for a sensor 10 with large dead volumes. One may first purge reservoir 24 and sensor 10 with valves 25 and 26 having positions 1,1, respectively. Second, the reservoir 24 and sensor 10 may be evacuated with valve 25 and 26 positions, respectively, 2,3, 2,2 or 2,1. Third, the preconcentrator (PC) 11 sampling time may be taken with positions 3,2 of valves 25 and 26, respectively. Fourth, the analyte 30 in PC 11 may be desorbed while valves 25 and 26 having positions 3,2, respectively. Fifth, a PC 11 analyte 30 pulse 27, having a width of a delta time ($\Delta t$) 37, may be injected into reservoir 24 with valves 25 and 26 having positions, respectively, 1,2 or 1,3 (for a few milliseconds). The first through fifth steps may be repeated until reservoir 24 is filled. Sixth, the analyte from reservoir 24 may be measured with positions 1,1 of valves 25 and 26, respectively. One may continue by returning to the first step.

In the present case, the whole PHASED chip may be used as a PC 11, e.g., with its elements connected in parallel. Alternatively, a small, heatable, stainless (or other material) tube coated (preferably) or packed with Tenax™ on its internal walls of the PC 11, may be used as a preconcentrator and modulator in FIG. 3. The reservoir 24 may be fashioned as simple empty containers of volume commensurate with the dead-volume of the sensor 10. But the containers may also feature some loose packing in a long tube that would enable the volume of the repeatedly injected analyte pulses 27 to gradually progress from an inlet 28 towards an outlet 29 in the manner of so-called "plug-flow", and thus require less of a vacuum at the start of the process. In addition, another approach is that the second valve 26 (between the reservoir 24 and the sensor 10) may have an opening to the ambient or sample gas, so that the gas may be sampled by the sensor 10 directly, without the need for pre-concentration, in a situation where the analyte 30 concentrations are much higher than the MDL.

Depending on what one might know about the portion of the gas absorbed and the level of concentration, the arrangement of a sensor system 20 may be used for sensor calibration or for end-of-life testing.

Figure 3A:
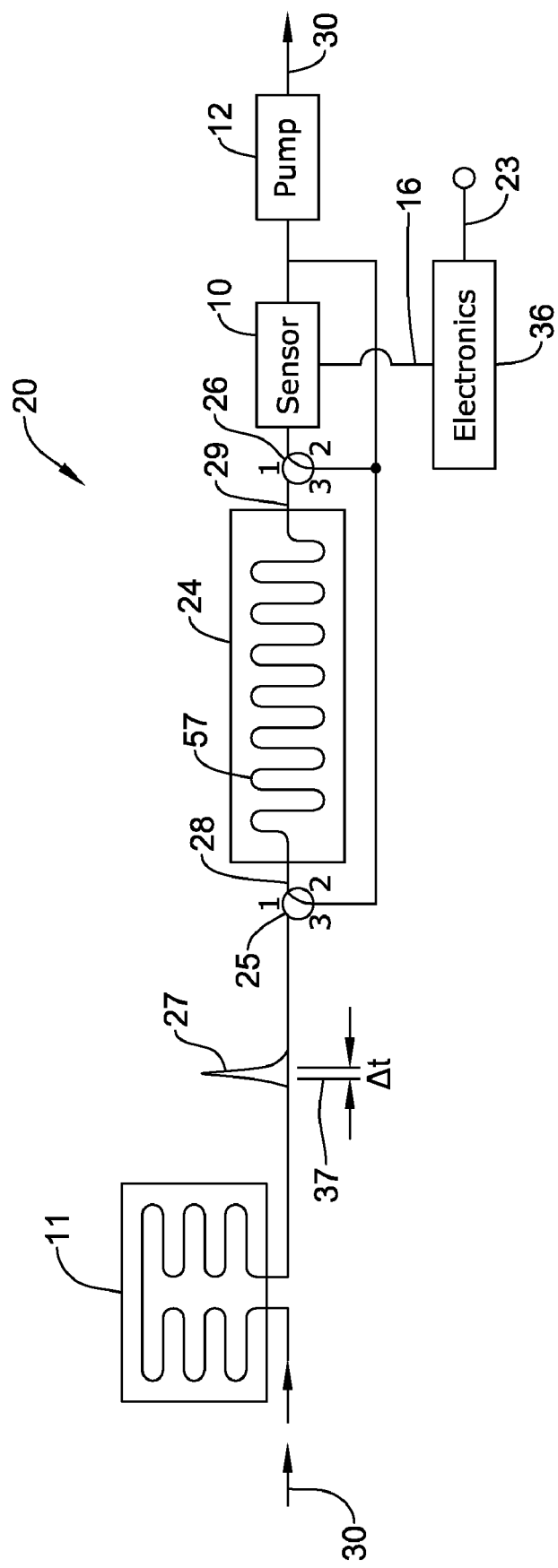
FIG. 3a is a diagram of a sensor system having a pre-concentrator analyte modulator arrangement with a reservoir having a long tubular shape.

FIG. 3a shows another version of the sensor system 20 with an input sample of about 10 mm$^3$/sec to the modulator 11 which is connected to reservoir 24 as in FIG. 3. FIG. 3a shows reservoir 24 having a long tubular shape to minimize mixing of new analyte pulses with previous pulses 27, while still facilitating an increase of sensitivity of the detector 10, due to the increased concentration of analyte from the modulator 11. In other words, the reservoir 24 may have the shape of a long and narrow tubing to minimize mixing of new gas with old gas.

Figure 3B:
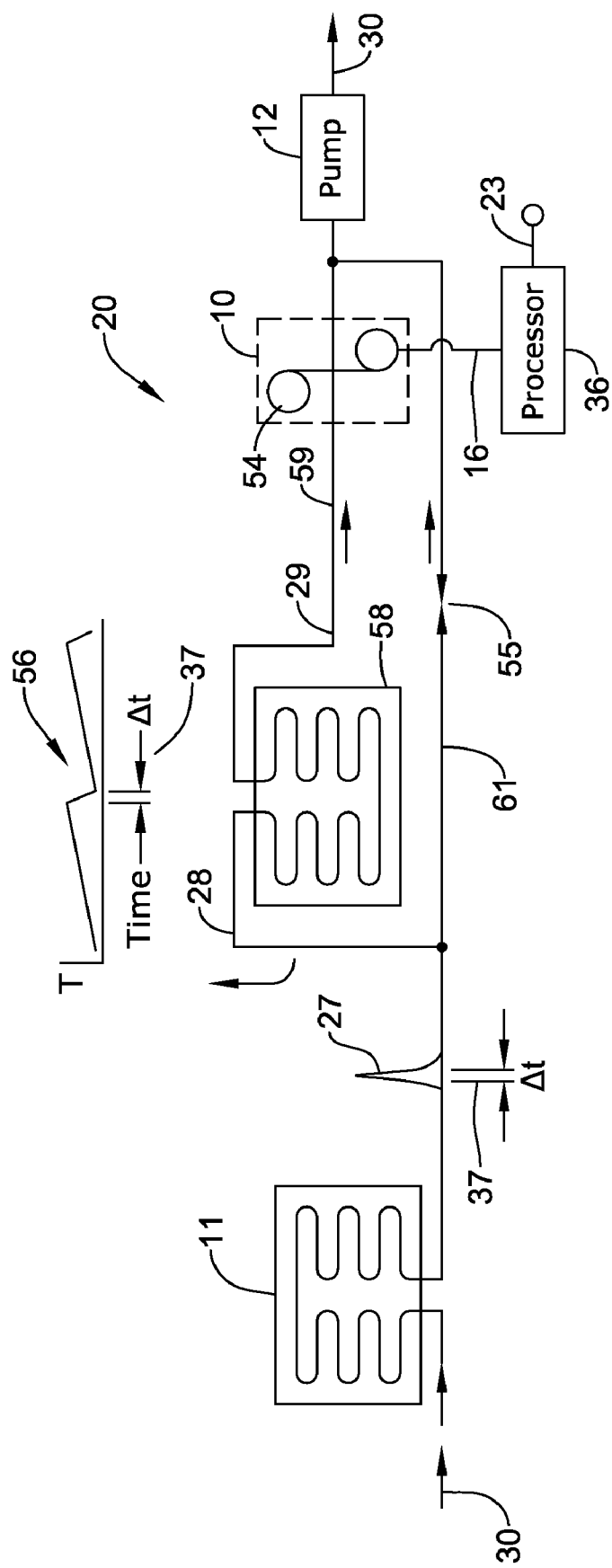
FIG. 3b is a diagram of a sensor system like that of FIG. 3 in which the reservoir and valves have been replaced by a rapidly heatable reservoir.

FIG. 3b is a diagram of another approach of the sensor system 20 in which the reservoir 24 and valves 25 and 26 have been replaced by a rapidly heatable reservoir 58, which pulls each pre-concentrated Δt-peak 27 into the "high concentration path" 59 by way of suitably synchronized slow heating and rapid cooling periods. An output of reservoir 58 may provide about 0.9 mm$^3$/sec concentration flow through line 59 to a sensor 54, for which a paper type sensor is selected for this illustrative example. Other types of sensors may be selected also. Bypassing input 28 of reservoir 58 may be a low concentration 9 mm3/sec flow through line 61 to pump 12 via a restriction 55. The restriction 55 in the low-concentration bypass can facilitate adjustment and balancing of the flow, so that (in present example) the high-concentration flow in line 59 may be about 10 times smaller than the bypass flow.

During soaking and PC time, the reservoir gas temperature may rise and expand (insert 56) to prevent low concentration gas from entering. As to volume (V) dynamics of reservoir 58, a peak volume may be VΔt and the reservoir volume may be 1-10×VΔt. The reservoir 58 "suction" pump rate (during rapid gas cooling) may be minus 10 mm$^3$/sec for about 1 Δt and the "expansion" rate (slow heating) may be plus 1 mm$^3$/sec for a time of about 10 Δt.

It could be said that the valves may be eliminated in the system 20 of FIG. 3b since, in lieu of reservoir 24, reservoir 58 is a heatable version with a similar long and narrow tube, which may be operated (by cooling and heating) to draw the modulator gas pulse 27 into the reservoir when rapidly cooled, and slowly heated to expand the gas to match the sample flow rate to the pump 12 and the substantially zero flow rate input from the modulator 11 during the time when the modulator is in its adsorption period or mode.

The "sensor" or detector 10 of system 20 in FIG. 3b may be one of numerous types, such as an electrochemical, microdischarge detector (MDD), a flame ionization detector (FID), a thermal conductivity detector (TCD), a chemical impedance detector (CID), and a paper tape detector (PTD) 54.

Figure 4:
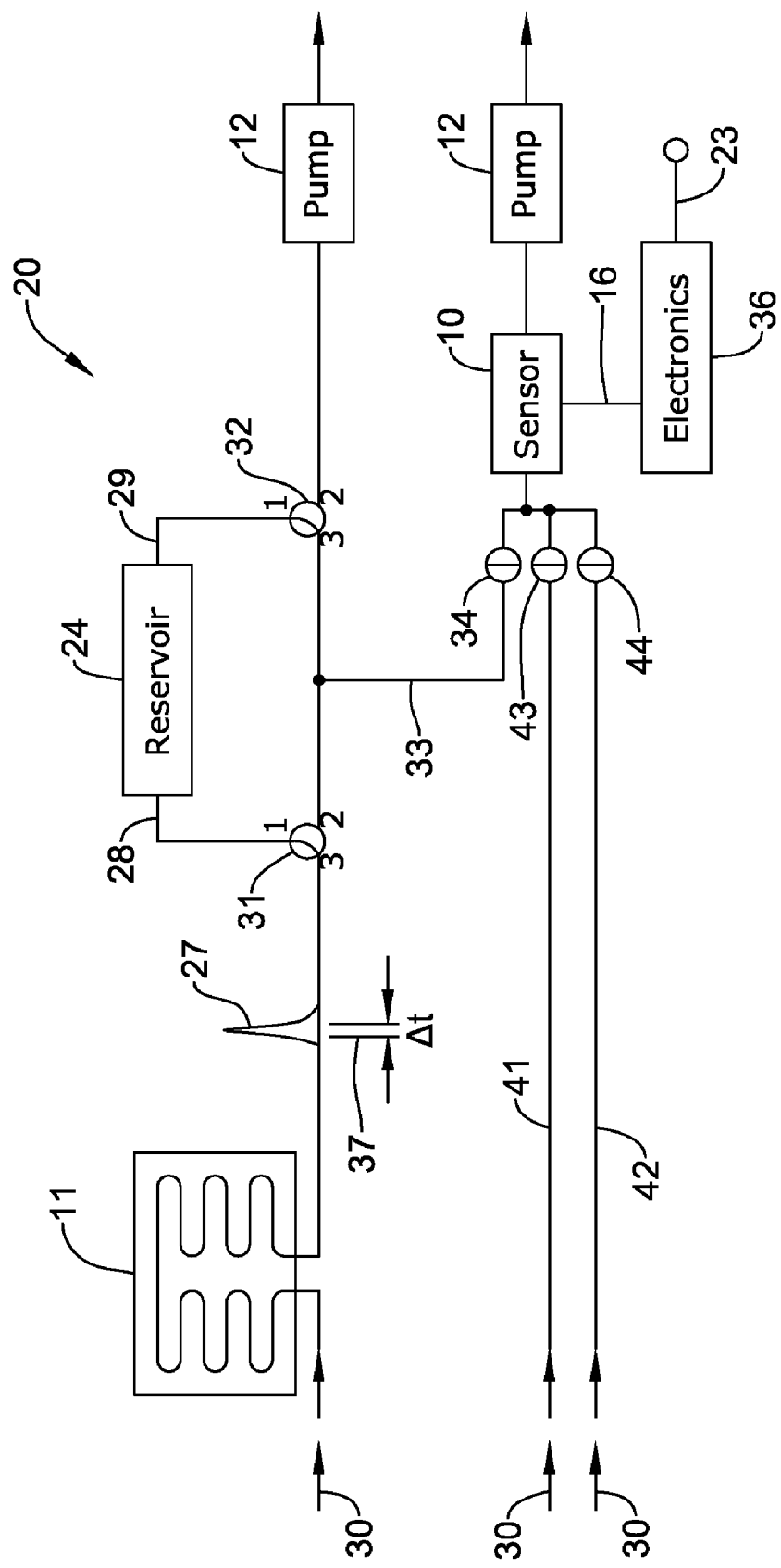
FIG. 4 is a diagram of a sensor system like that of FIG. 3 but having a different connection configuration and additional sample lines.

FIG. 4 is a diagram of a pre-concentration approach for sensors 10 having large off-times or large dead volumes. It may illustrate how the accumulation of analyte 30 in a reservoir 24 can help the use of available off-time of a multi-sample gas stream, to accumulate analyte 30, which otherwise would require a much larger measurement time. First, the reservoir 24 may be evacuated with positions 1,2 and 1,2 for valves 31 and 32, respectively. Second, a stream in line 33 may be sampled with valve 34 off and with valves 31 and 32 having positions 3,2 and 3,2, respectively. Third, a peak or pulse 27 may be captured within a time 37 (Δt) with the valves 31 and 32 having positions 3,1 and 3,2, respectively. The second and third steps may be repeated until reservoir 24 is filled. Fourth, valve 34 may be opened and the reservoir gas may be sensed with the valves 31 and 32 in positions 3,1 and 3,1, respectively. Other sample lines 41 and 42 with analyte 30 may go to sensor 10 via valves 43 and 441 respectively. As needed, pumps 12 may maintain a movement of the analyte 30.

The present sensor system 20, whether mass flow-dependent or not, may have a MEMS adsorber-film-coated, heatable, flow-through preconcentrator (PC) 11 upstream of a sensor 10, or a packed adsorber, heatable, flow-through preconcentrator (PC) 11 upstream of a sensor 10 and a mechanism to transport a flow sample through a preconcentrator 11 and through the sensor 10, and generate analyte concentration pulsations by heating the PC 11 film in a periodic manner, while sample gas or analyte 30 is flowing. Sensor system 20 may also leverage the concentration or flow rate modulation to generate chopped DC or (preferred) AC-modulated sensor output 16 signals, which can be amplified and segregated or filtered (for example, with short time constant detection, high-pass, AC coupling, synchronous amplification, or other approaches) with electronics 36 and thus minimize the effect of baseline drift and increase the sensor's achievable S/N (signal-to-noise ratio) and thus reduce its MDL (minimum detectable limit). Sensor system 20 may use, first, discrete components comprising an adsorber 14, a reservoir 24 (or not), a sensor 10, and off-the-shelf pump 12, or second, integrated components comprising an adsorber 14 (e.g., a PHASED chip), a sensor 10 (such as thermal conductivity, polymer-film, electrochemical and/or micro-discharge detectors), and an integrated thermal pump 12 to bring about such sensor signal modulation and sample transport on one chip. Certain discrete or integrated components may make up the analyte modulator 11 which can be the PC 11.

The sensor system 20 with an analyte modulator 11 may substantially reduce the effect of a sensor's baseline drift relative to a comparable sensor system without such a modulator. The analyte concentration modulator 11 may increase the reliability of the sensor system 20 and improve its MDL. If a thermal pump is selected for operation with the subject sensor system 20, one may more easily integrate pump 12, PC 11, separator, and possibly a sensor 10 within a "lab-on-a-chip" structure that has a lower fabrication cost (since many assembly steps are performed at the wafer level), more compact packaging and a faster response (important for first responders) than other implementations of the system in FIG. 1 based on off-the-shelf discrete components. A thermal pump should reduce the needed operating voltage relative to electrostatic-driven pumps and may be manufacturable on a monolithic "PC+pump+sensor" chip, with an already integrated TCD and flow sensor.

The sensor system 20 in FIG. 3 may enable evacuation and storage of preconcentrated analyte 30 in a reservoir 24 for more sensitive measurements overcoming a mismatch between sensor dead volume and PC 11 analyte pulse volume, and/or facilitating dosimetry of very low concentrations, which may be too small to sense directly, without pre-concentration.

An idea of collecting "puffs" into a MEMS vessel to solve a mismatch may be different and separate from the dosimeter idea. A dosimeter does not necessarily rely on such idea to work. The idea of collecting puffs and releasing them later may be well suited to paper-tape type and like analyzers that have large volume requirements but relatively an infrequent need to measure (because analyte concentrations do not change rapidly and more than one location may need to be monitored (multi-stream)).

Figure 6:
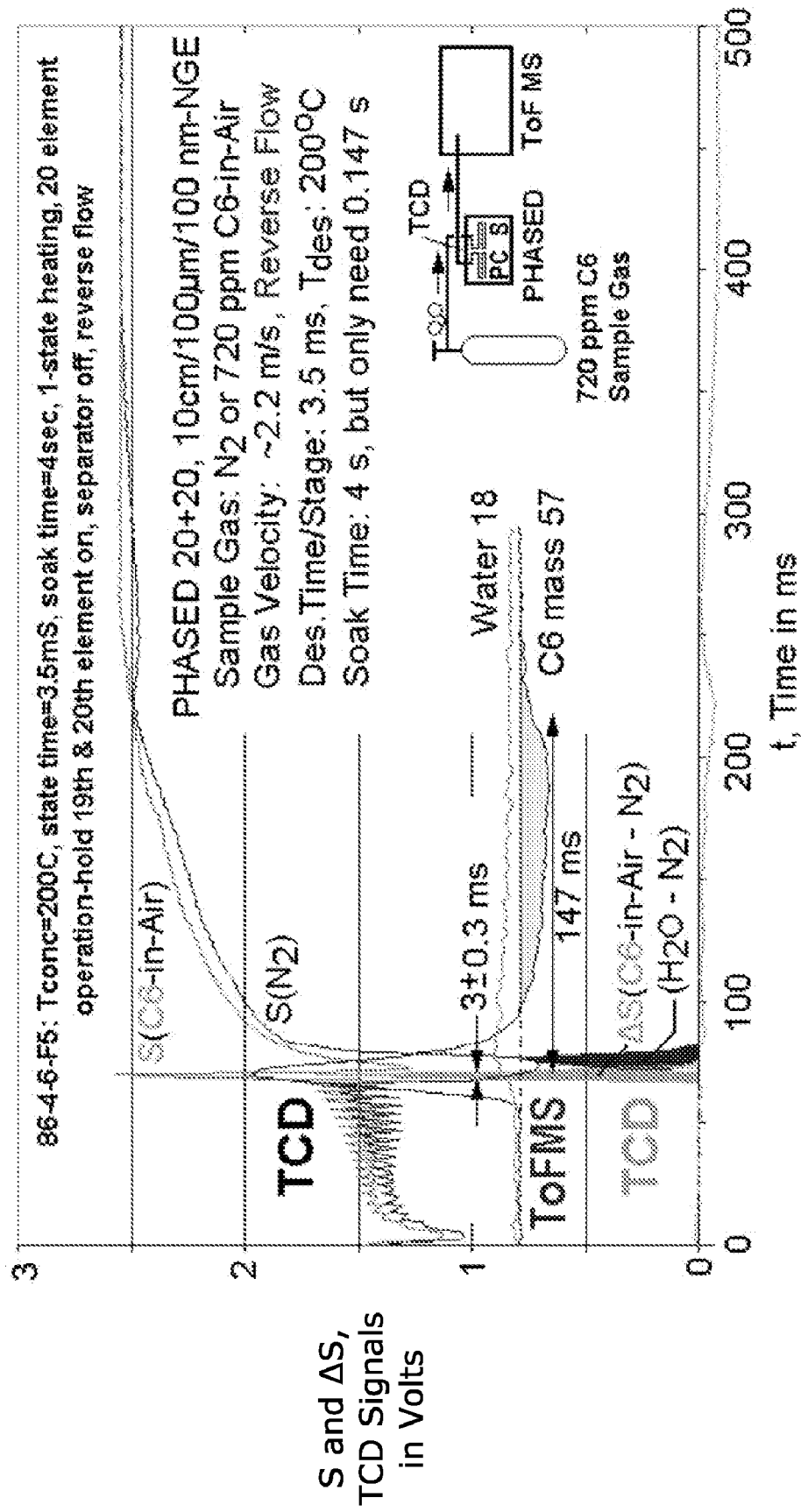
FIG. 6 is a graph like that of FIG. 5 but for an adsorption period longer than a desorption period of a complete cycle.
Figure 7:
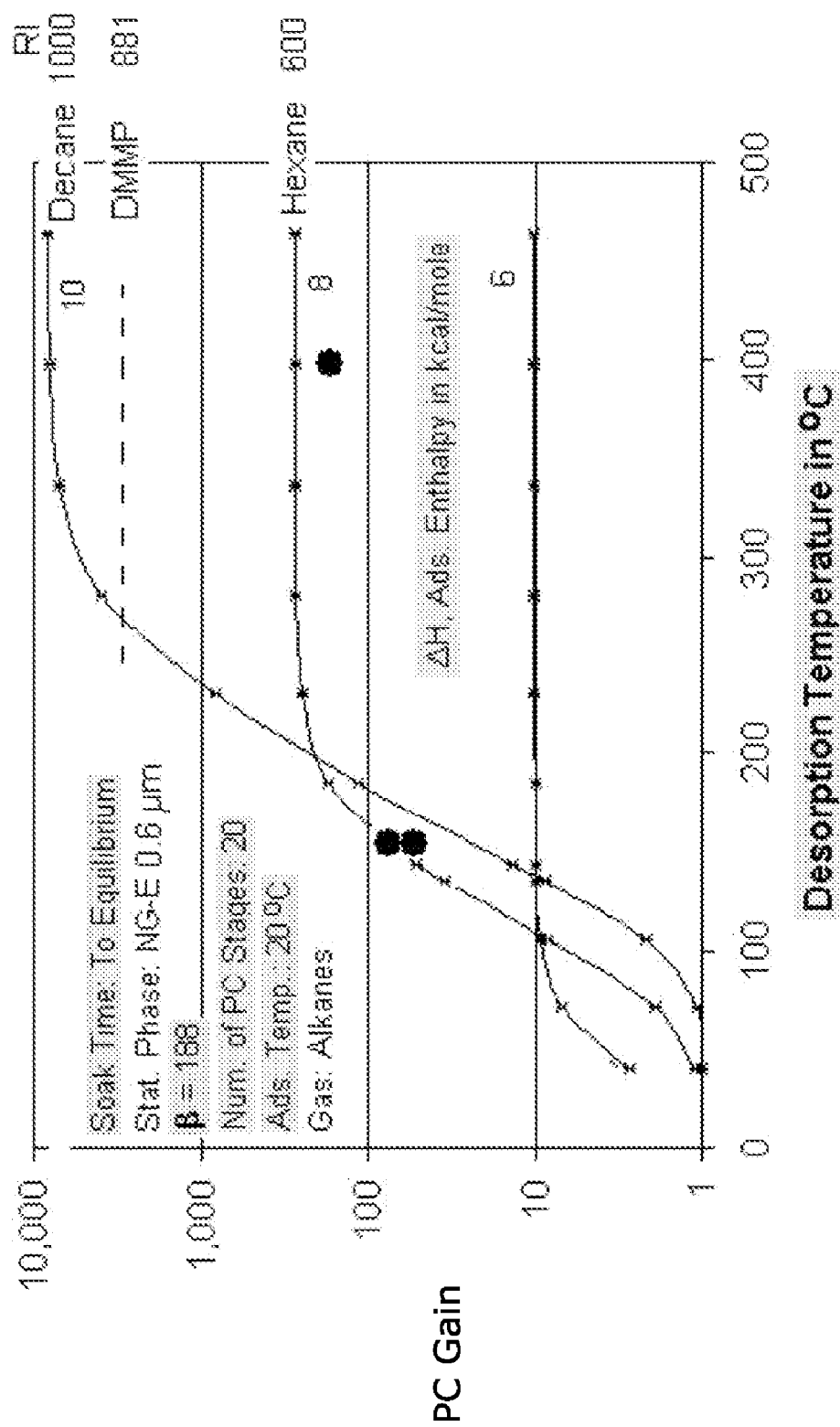
FIG. 7 is a graph showing gain variability for a typical set of pre-concentrator parameters of a system like that of FIGS. 1, 3 and 4.
Figure 8:
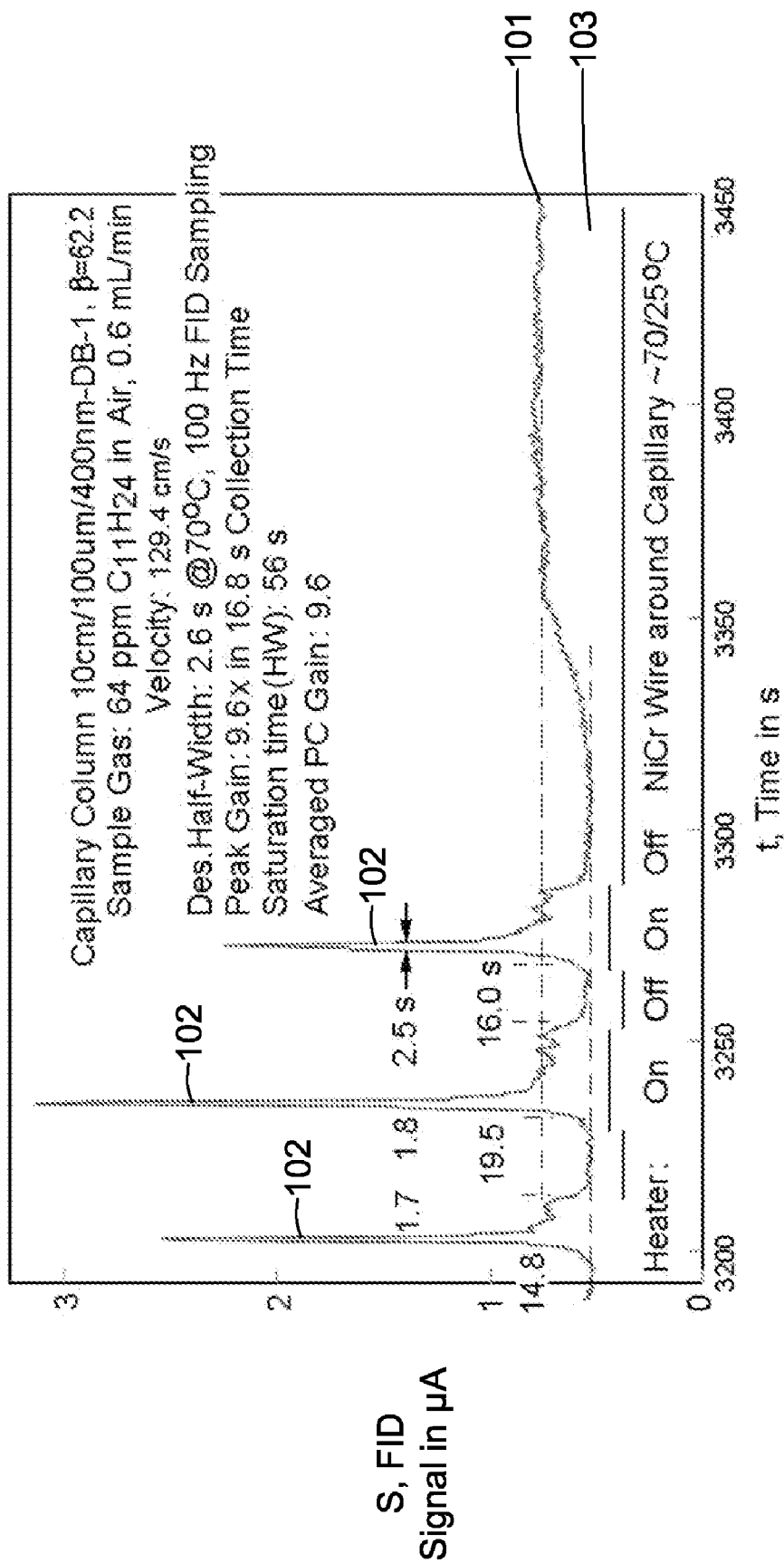
FIG. 8 is a graph of a pre-concentrator gain involving a coated capillary.

FIGS. 5-8 show examples of the adsorption and desorption during pre-concentration action. The PC 11 may be either part of PHASED with Nanoglass™ as the adsorber film (FIGS. 5-7) or a PDMS-coated capillary (FIG. 8). PDMS may be polydimethylsiloxane (viz., silicone rubber). The analyte 30 was 720 ppm for hexane in air for FIGS. 5-7 and 64 ppm undecane in air for FIG. 8. The Figures, and particularly FIG. 8, show three concentration levels of analyte. A first level, 101, may flow through the preconcentrator 11 to the detector (a time-of-flight mass spectrometer and TCD (thermal conductivity detector) for FIGS. 7 and 8 and an FID (flame ionization detector) for FIG. 8), while the adsorber 14 may be maintained at an elevated temperature for some extended period of time, so that no adsorption occurs. A second and much higher concentration, 102, may be measured when the PC 11 is rapidly heated, generating a desorption "peak". A third near zero concentration (or depletion peak), 103, may be measured when the PC 11 is at low temperature just after the desorption, showing that essentially no analyte is reaching the sensor 10 until the breakthrough time, which appears to be about 0.3, 0.147 and 56 seconds for FIGS. 5, 6 and 8, respectively. These examples illustrate the PC 11 operation as practiced for gas chromatography, where obtaining high and narrow desorption peaks appears highly desirable and the detectors used may be groomed to have a very small dead-volume. The dead volume may be larger with other sensors intended for use in the present application. In the application, the PC 11 desorption and adsorption periods may be controlled to suppress the "pass through" concentration of analyte 30 of the first level, so that the sensor 10 may be only exposed to the concentrations of the second and third levels. This may be achieved by heating the PC 11 just before an analyte "break-through".

Figure 5:
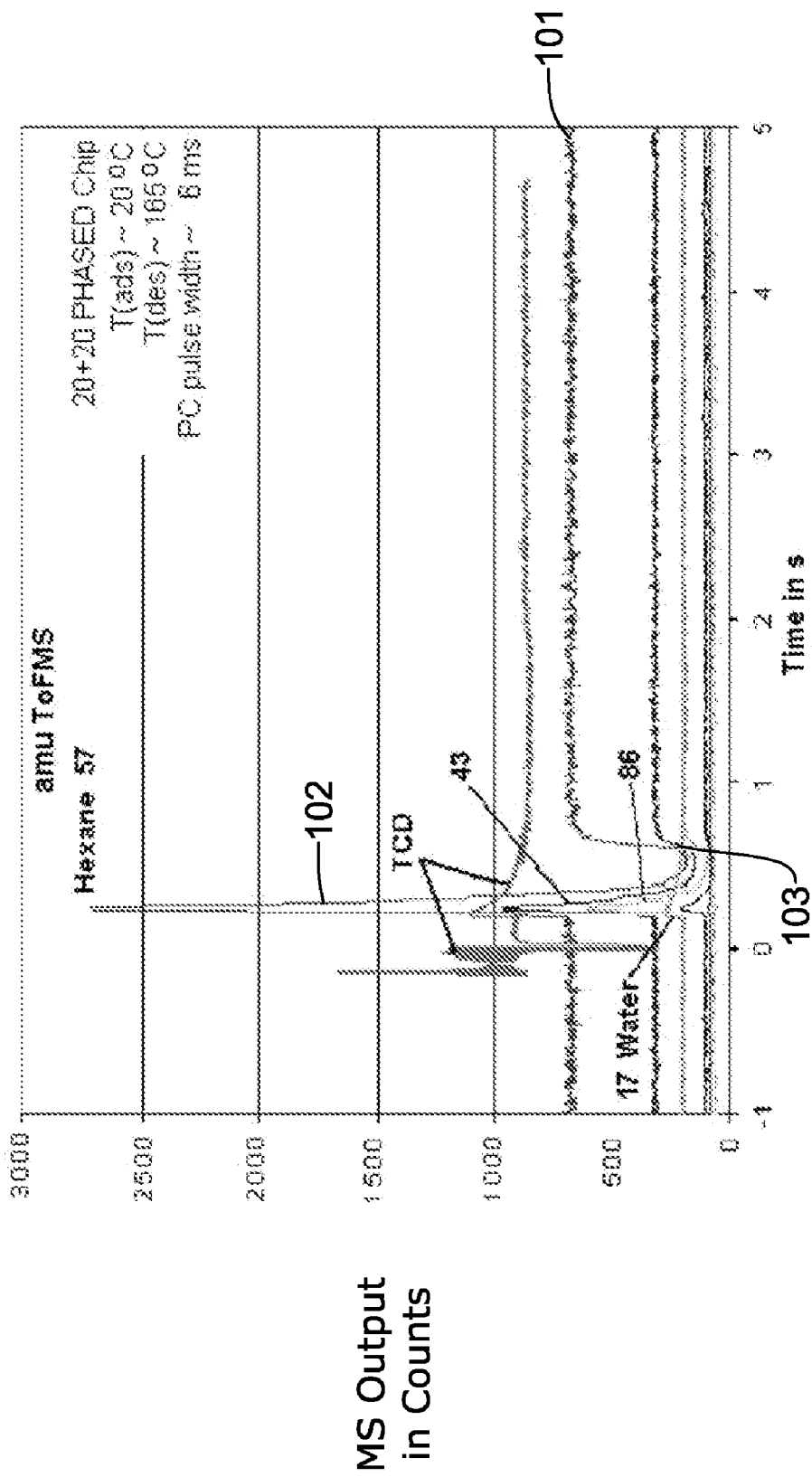
FIG. 5 is a graph of a desorption and adsorption cycle, with several analyte concentration levels, and sensor outputs for a pre-concentration, separation and component analysis of a fluid.

FIG. 5 shows one desorption and adsorption cycle, with three distinct analyte concentration levels, using a TCD and ToFMS to generate the sensor outputs for a 20-Stage PHASED pre-concentration and separation analysis of a 720 ppm hexane-in-air sample gas at about 60 cm/s sample gas velocity in the 100×100-μm PHASED channels. TCD refers to thermal conductivity detector, TOFMS refers to a time-of-flight mass spectrometer by Leco, and amu refers to atomic mass units.

FIG. 6 shows one desorption and adsorption cycle, with the three distinct analyte concentration levels, using TCD and TOFMS to generate the sensor outputs, also indicating as in FIG. 5, that the adsorption period may be longer than the desorption period of the complete cycle. Also listed are experimental parameters related to the adsorber geometry (10 cm in length, 100 um of inner channel size and 100 nm of adsorber film thickness (NGE), desorption temperature (200 deg. C.) and average sample gas velocity (2.2 m/s), which may influence PC 11 gain. Such gain variability, for a typical set of PHASED parameters, is shown in FIG. 7. One may have 20 stages, 600-nm of Nanoglass™ adsorber film and β=188 (gas/film volumetric ratio). FIG. 6 shows a PHASED sample collection, pre-concentration and separation, demonstrated with 720 ppm hexane- and water-in-air sample gas. Time to fill the PC may be about 147 msec. Also shown is a PC 11 concentration gain of about 1.70/(0.022±50%)=77. A thicker PC film than the 100-nm Nanoglass™ may increase the fill time and the PC gain. FIG. 8 shows a pre-concentration gain demonstrated with a DB-5-coated capillary, using a 64 ppm undecane-in air sample gas at about 129.4 cm/s, leading to a 56 second breakthrough time. FIG. 8 further shows a measured repetition of three cycles of adsorption and desorption obtained with the PDMS-coated capillary.

Figure 9:
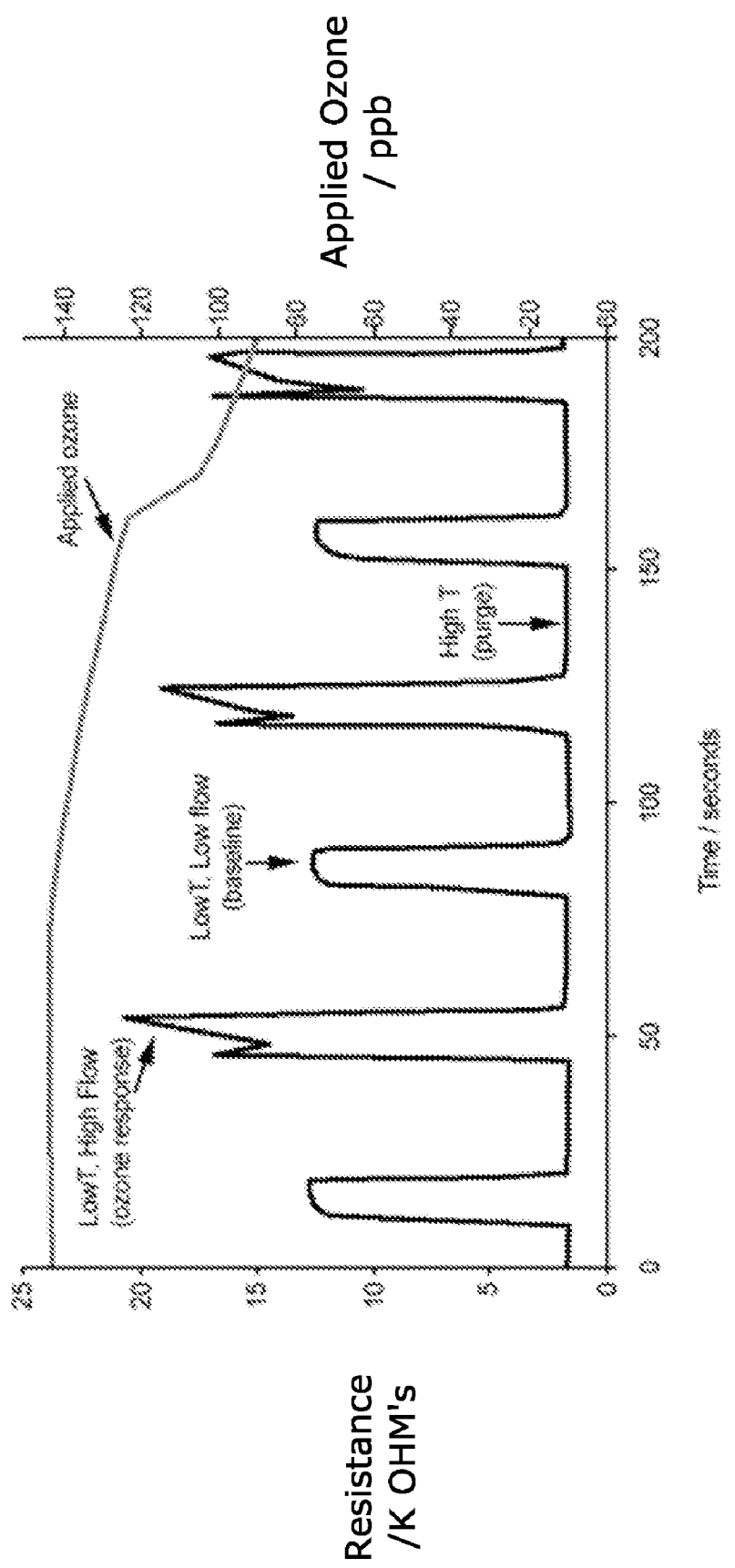
FIG. 9 shows sensor data of a flow rate being periodically interrupted to show an example of a baseline.

FIG. 9 is a graph of an ozone sensor output reflecting a flow rate periodically interrupted to show an example baseline.

Figure 10:
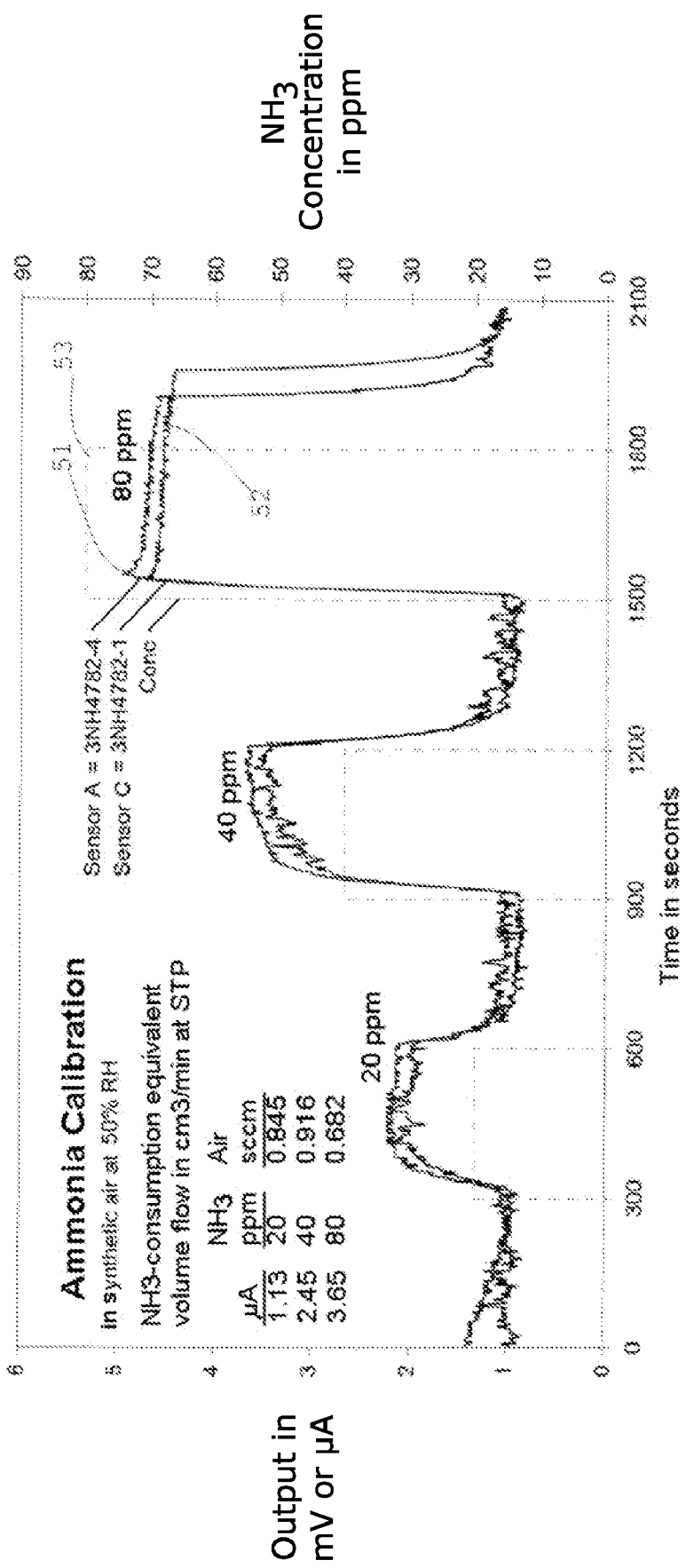
FIG. 10 is a graph of a calibration and response time of several electrochemical detectors of ammonia.

FIG. 10 is a graph of a calibration and response time of two electrochemical (EC) detectors of ammonia, with curves 51 and 52 showing good repeatability, and an increase of the detector signals as the set concentrations 53 (dashed lines) are increased (with output instances of 1.13 μA, 2.45 μA and 3.65 μA, for 20, 40 and 80 $NH_3$ ppm concentrations with air sccm of 0.845, 0.916 and 0.682, respectively, relative to time) and a response time of about 90 sec. Indicated in the graph is the measured ammonia consumption of a detector in terms of equivalent volume flow in $cm^3$/min or sccm, which may influence the noted response time.

Figure 11:
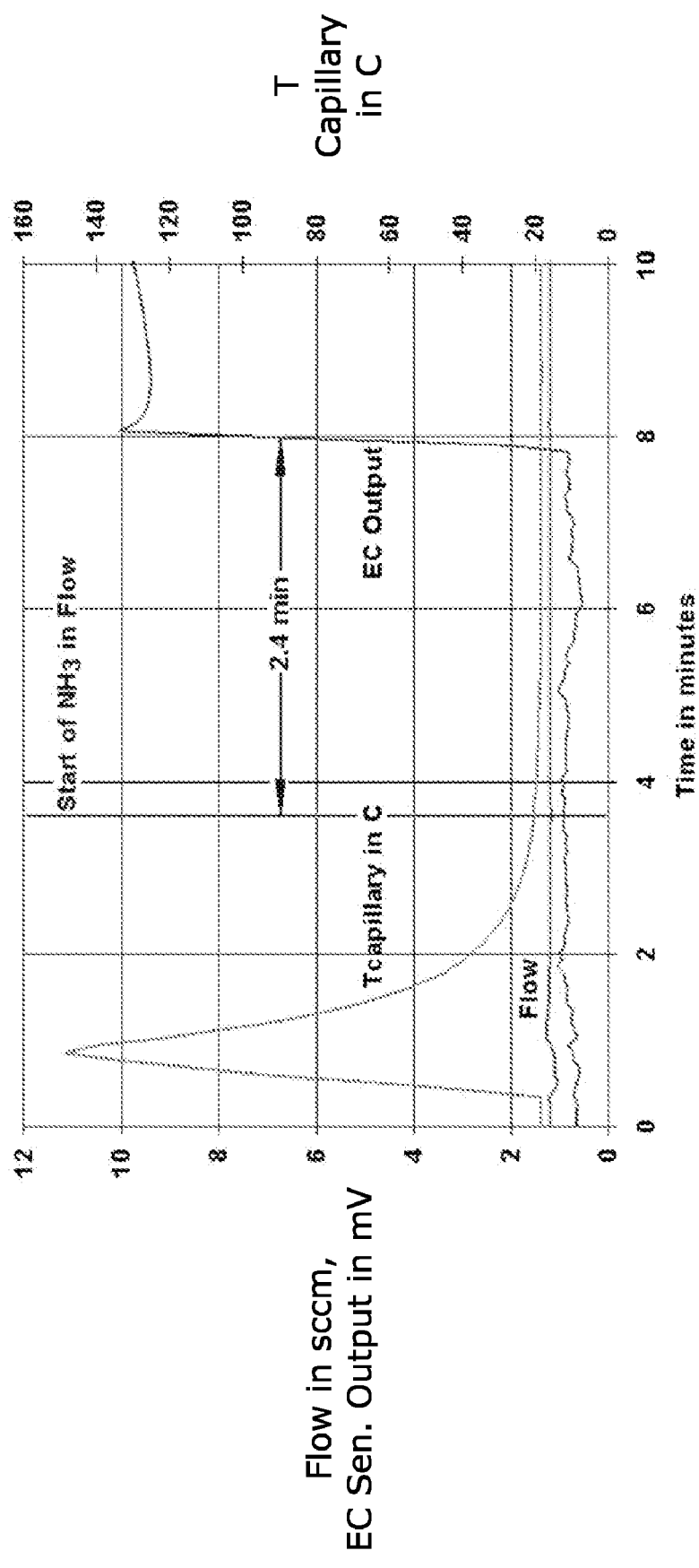
FIG. 11 is a graph of an example modulator breakthrough measurement.

FIG. 11 is a graph of a modulator 11 breakthrough measurement. After an initial heating of a capillary column to 150 deg C., $NH_3$ gas of about 60 ppm may be applied to the column for a time=3.6 min, after which the breakthrough appears to occur at about 7 min, so that the total breakthrough time becomes about 2.4 min representing 50 "air changes." The $NH_3$ concentration can be about 60 ppm, but its value may not necessarily influence the breakthrough time herein, which, as intended, appears larger than the 60 to 100 sec response time of an EC cell of FIG. 10, and much larger than a PHASED modulator 11 chip breakthrough times. Other parameters of the graphed demonstration may include a flow=1.3 sccm, heatable stainless steel capillary length=28.5 cm, ID=0.53 mm, volume=0.0628 $cm^3$ and packing=Hayesep "P" μspheres, flow rate=0.0217 $cm^3$/sec, and 1 air purge frequency every 2.90 sec.

Figure 12:
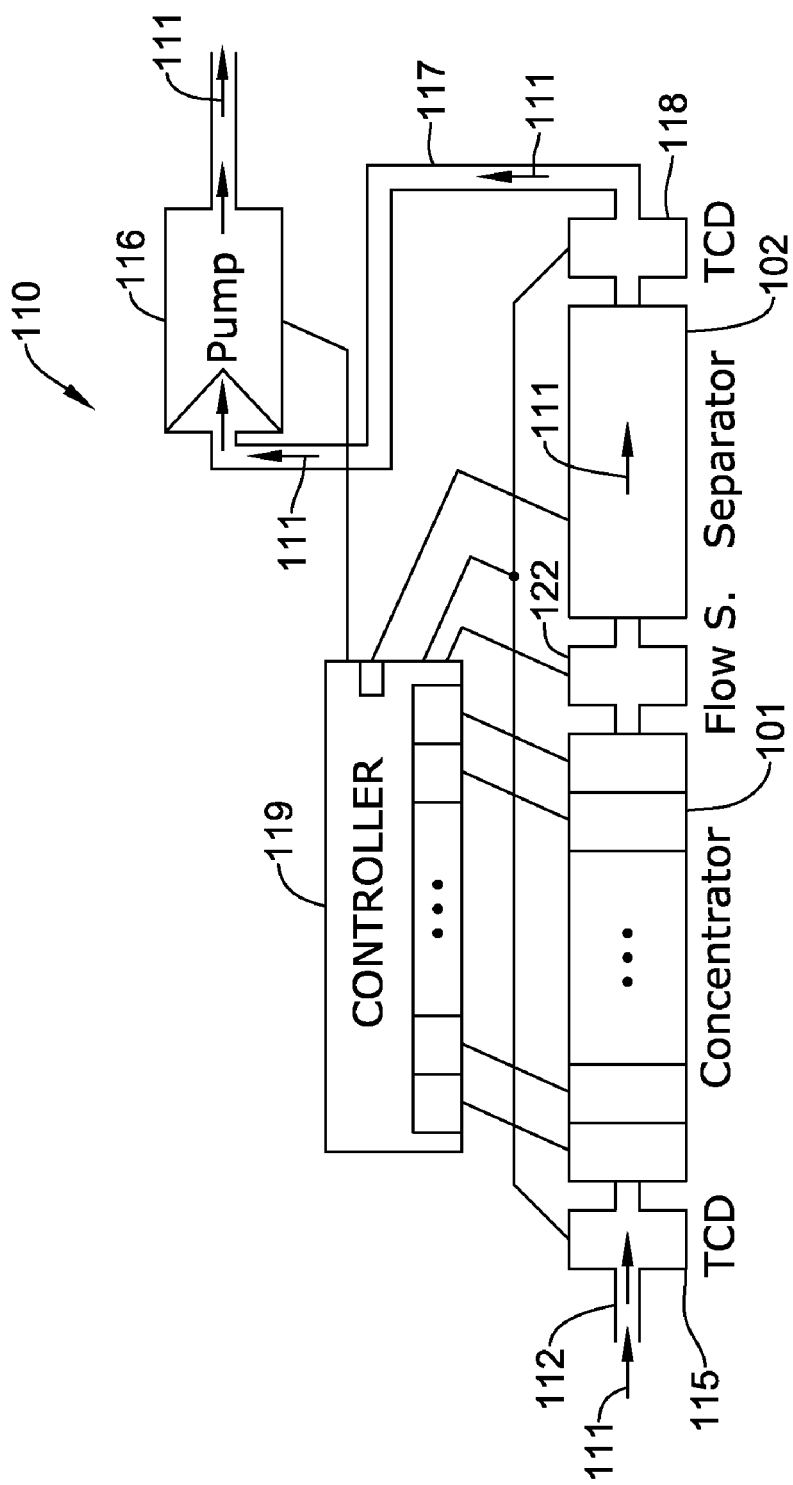
FIGS. 12-15 show an illustrative example of a pre-concentrator that may be used as an analyte modulator for the present sensor system.

A fluid analyzer which may be used for an analyte modulator 11 in conjunction with the sensor system 20 may include a channel or channels for a flow of a sample along a membrane that supports heaters and a stationary phase for sample analysis. The channel or channels may be an integral part of the micro fluid analyzer. The analyzer may have the pre-concentrator (PC) 101 (i.e., like that of PC 11) and chromatographic separator (CS) 102 which incorporates the channel or channels. FIG. 12 is a system view of an example fluid analyzer which may be a phased heater array structure for enhanced detection (PHASED) micro gas analyzer (MGA) 110. It reveals certain details of the micro gas apparatus 110 which may encompass the specially designed channel described herein. The PHASED MGA 110, and variants of it, may be used for various fluid chromatography applications.

Sample stream 111 may enter input port 112 to the first leg of a differential thermal-conductivity detector (TCD) (or other device) 115. A pump 116 may effect a flow of fluid 111 through the apparatus 110 via tube 117, though pump 116 may be a thermal pump or be replaced by a thermal pump. There may be additional pumps, and various tube or plumbing arrangements or configurations for system 110 in FIG. 12. Fluid 111 may be moved through a TCD 115, concentrator 101, flow sensor 122, separator 102 and TCD 118. Controller 119 may manage the fluid flow, and the activities of concentrator 101 and separator 102. Controller 119 may be connected to TCD 115, concentrator 101, flow sensor 122, separator 102, TCD 118, and pump 116. The pump 116 may be a thermal pump or be replaced with a thermal pump integrated in the concentrator 101 or separator 102. Data from detectors 115 and 118, and sensor 122 may be sent to controller 119, which in turn may process the data. The term "fluid" used herein may refer to a gas or a liquid, or both.

Figure 13:
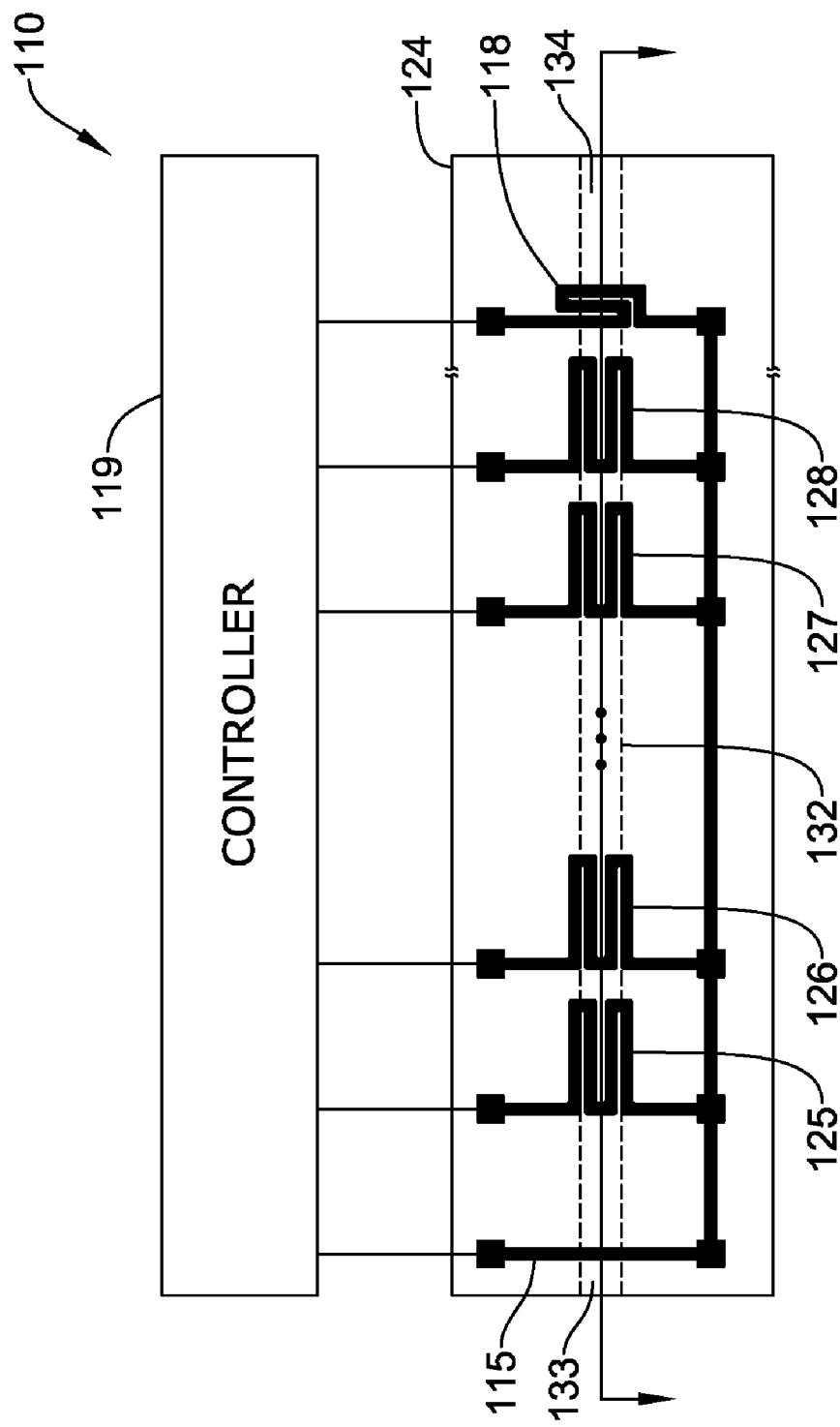

FIG. 13 is a schematic diagram of part of the sensor apparatus 110 representing a portion of concentrator 101 and/or separator 102 in FIG. 12. This part of sensor apparatus 110 may include a substrate or holder 124 and controller 119. Controller 119 may or may not be incorporated into substrate 124. Substrate 124 may have a number of thin film heater elements 125, 126, 127, and 128 positioned thereon. While only four heater elements are shown, any number of heater elements may be provided, for instance, between two and one thousand, but typically in the 20-100 range. Heater elements 125, 126, 127, and 128 may be fabricated of any suitable electrical conductor, stable metal, alloy film, or other material. Heater elements 125, 126, 127, and 128 may be provided on a thin, low-thermal mass, low-in-plane thermal conduction, membrane or support member 124, as shown in FIGS. 13 and 14.

Figure 14:
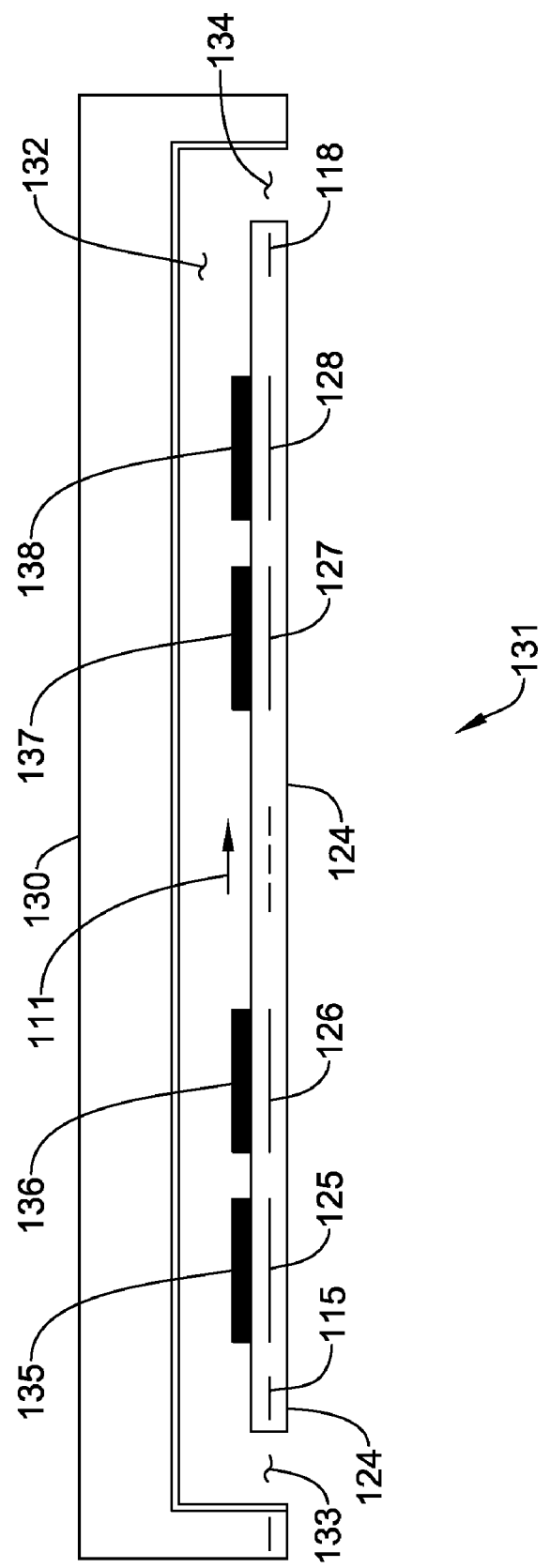

Substrate 130 may have a well-defined single-channel phased heater mechanism 131 having a channel 132 for receiving the sample fluid stream 111, as shown in FIG. 14. The channels may be fabricated by selectively etching silicon channel wafer substrate 130 near support member 124. The channel may include an entry port 133 and an exhaust port 134.

The sensor apparatus 110 may also include a number of interactive elements inside channel 132 so that they are exposed to the streaming sample fluid 111. Each of the interactive elements may be positioned adjacent, i.e., for closest possible contact, to a corresponding heater element. For example, in FIG. 14, interactive elements 135, 136, 137, and 138 may be provided on a surface of support member 124 in channel 132, and be adjacent to heater elements 125, 126, 127, and 128, respectively. There may be other channels with additional interactive film elements which are not shown in the present illustrative example. The interactive elements may be formed from any number of films commonly used in liquid or gas chromatography. Furthermore, the above interactive substances may be modified by suitable dopants to achieve varying degrees of polarity and/or hydrophobicity, to achieve optimal adsorption and/or separation of targeted analytes.

Controller 119 may be electrically connected to each of the heater elements 125, 126, 127, 128, and detectors 115 and 118 as shown in FIG. 13. Controller 119 may energize heater elements 125, 126, 127 and 128 in a time phased sequence (see bottom of FIG. 15) such that each of the corresponding interactive elements 135, 136, 137, and 138 become heated and desorb selected constituents into a streaming sample fluid 111 at about the time when an upstream concentration pulse, produced by one or more upstream interactive elements, reaches the interactive element. Any number of interactive elements may be used to achieve the desired concentration of constituent gases in the concentration pulse. The resulting concentration pulse may be provided to detector 118, for detection and analysis.

Figure 15:
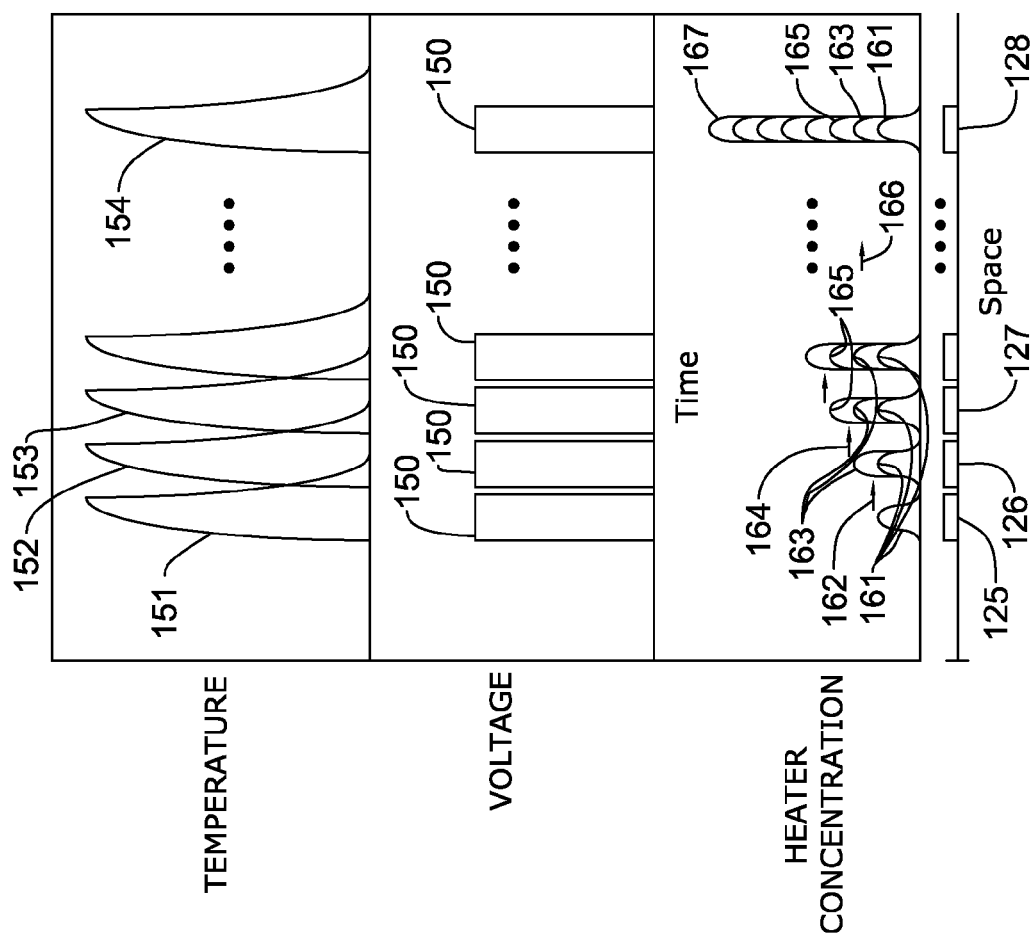

FIG. 15 is a graph showing illustrative relative heater temperatures, along with corresponding concentration pulses produced at each heater element. As indicated above, controller 119 may energize heater elements 125, 126, 127 and 128 in a time phased sequence with voltage signals 150. Time phased heater relative temperatures for heater elements 125, 126, 127, and 128 may be shown by temperature profiles or lines 151, 152, 153, and 154, respectively.

In the example shown, controller 119 (FIG. 13) may first energize first heater element 125 to increase its temperature as shown at line 151 of FIG. 15. Since first heater element 125 is thermally coupled to first interactive element 135 (FIG. 14), the first interactive element desorbs selected constituents into the streaming sample fluid 111 to produce a first concentration pulse 161 (FIG. 15) at the heater element 125, if no other heater elements were to be pulsed. The streaming sample fluid 111 carries the first concentration pulse 161 downstream toward second heater element 126, as shown by arrow 162.

Controller 119 may next energize second heater element 126 to increase its temperature as shown at line 152, starting at or before the energy pulse on element 125 has been stopped. Since second heater element 126 is thermally coupled to second interactive element 136, the second interactive element also desorbs selected constituents into streaming sample fluid 111 to produce a second concentration pulse. Controller 119 may energize second heater element 126 such that the second concentration pulse substantially overlaps first concentration pulse 161 to produce a higher concentration pulse 163, as shown in FIG. 15. The streaming sample fluid 111 may carry the larger concentration pulse 163 downstream toward third heater element 127, as shown by arrow 164.

Controller 119 may then energize third heater element 127 to increase its temperature as shown at line 153 in FIG. 15. Since third heater element 127 is thermally coupled to third interactive element 137, third interactive element 137 may desorb selected constituents into the streaming sample fluid to produce a third concentration pulse. Controller 119 may energize third heater element 127 such that the third concentration pulse substantially overlaps larger concentration pulse 163 provided by first and second heater elements 125 and 126 to produce an even larger concentration pulse 165. The streaming sample fluid 111 carries this larger concentration pulse 165 downstream toward an "Nth" heater element 128, as shown by arrow 166.

Controller 119 may then energize "N-th" heater element 128 to increase its temperature as shown at line 154. Since "N-th" heater element 128 is thermally coupled to an "N-th" interactive element 138, "N-th" interactive element 138 may desorb selected constituents into streaming sample fluid 111 to produce an "N-th" concentration pulse. Controller 119 may energize "N-th" heater element 128 such that the "N-th" concentration pulse substantially overlaps larger concentration pulse 165 provided by the previous N–1 interactive elements. The streaming sample fluid may carry the resultant "N-th" concentration pulse 167 to either a separator 102 or a detector 118.

In the present specification, some of the matter may be of a hypothetical or prophetic nature although stated in another manner or tense.

Although the invention has been described with respect to at least one illustrative example, many variations and modifications will become apparent to those skilled in the art upon reading the present specification. It is therefore the intention that the appended claims be interpreted as broadly as possible in view of the prior art to include all such variations and modifications.

What is claimed is:

1. A sensor system comprising:
    a sensor; and
    an analyte modulator having an output connected to an input of the sensor;
    wherein the analyte modulator modulates analyte at a first time constant, an output of the sensor has a drift at a second time constant, and the first time constant is shorter than the second time constant.

2. The system of claim 1, further comprising a mechanism for removing the drift at the second time constant from the output of the sensor.

3. The system of claim 2, further comprising a pump connected to the sensor for assuring a flow of the analyte.

4. The system of claim 2, wherein the analyte modulator provides adsorption and desorption to modulate the concentration of the analyte.

5. The system of claim 2, wherein the drift is a baseline drift.

6. The system of claim 2, wherein the analyte modulator is a heatable surface coated with an adsorber film.

7. The system of claim 2, wherein the analyte modulator is a PHASED concentrator or a heatable capillary.

8. The system of claim 2, wherein the mechanism for removing drift at a second time constant is an AC coupled amplifier or a synchronous amplifier.

9. The system of claim 2, further comprising a reservoir connected between the modulator and the sensor.

10. The system of claim 9, wherein the reservoir comprises long and narrow tubing, sufficient for drawing a gas pulse from the modulator into the reservoir when rapidly cooled, and sufficient for slowly heating the gas to be expanded to approximately match the sample flow rate to a pump and have a substantially zero flow rate input from the modulator while the modulator in is an adsorption mode.

11. The system of claim 9, further comprising:
a first multi-way valve connected between the modulator and the reservoir;
a second multi-way valve connected between the reservoir and the sensor; and
a bypass conveyance line connected to the first and second valves.

12. The system of claim 11, wherein the reservoir comprises long and narrow tubing sufficient for minimizing mixing of new gas with old gas.

13. A method for detection comprising:
providing an analyte sample;
detecting the analyte sample with a sensor that outputs a signal indicative of a parameter of the sample;
measuring a drift time constant of the signal;
modulating the analyte sample with a modulator at a modulation time constant prior to entry of the analyte sample into the sensor; and
removing a portion of the signal indicative of a parameter of the sample having a drift time constant.

14. The method of claim 13, wherein the modulation time constant is shorter than the drift time constant.

15. The method of claim 14, further comprising:
storing modulated analyte in a reservoir; and
detecting modulated analyte from the reservoir with the sensor.

16. The method of claim 15, further comprising:
purging the reservoir and sensor;
evacuating the reservoir and sensor;
taking a modulator sample time while the reservoir is not connected to the modulator;
desorbing the sample while the reservoir is not connected;
injecting a modulated analyte pulse into the reservoir while not connected;
repeating the preceding portion of this claim until the reservoir is adequately filled; and
detecting and/or measuring an analyte sample from the reservoir.

17. A system for measuring analyte, comprising:
a modulator for modulating analyte; and
a sensor for detecting analyte; and
a discriminator connected to the sensor;
wherein:
the modulator modulates the analyte with a signal having a first time constant;
a sensor output signal comprises a modulated analyte signal having a first time constant and a drift signal having a second time constant; and
the discriminator removes a signal having a second time constant from the sensor output signal.

18. The system of claim 17, wherein at least the modulator, the detector and filter are integrated components on one or more chips.

19. The system of claim 17, further comprising:
a first valve connected to the analyte modulator;
a second valve;
a reservoir having a first port connected to the first valve and a second port connected to the second valve;
an analyte conveyance line connected between the first and second valves; and
wherein an input of the detector is connected to the conveyance line at a place between the first and second valves.

* * * * *